US00PP20225P2

(12) United States Plant Patent
Smith

(10) Patent No.: US PP20,225 P2
(45) Date of Patent: Aug. 18, 2009

(54) *CHRYSANTHEMUM* PLANT NAMED 'COOL YOIGLOO'

(50) Latin Name: *Chrysanthemum×morifolium*
Varietal Denomination: Cool Yoigloo

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 12/214,251

(22) Filed: Jun. 16, 2008

(51) Int. Cl.
*A01H 5/00* (2006.01)

(52) U.S. Cl. ..... Plt./287

(58) Field of Classification Search ..... Plt./287
See application file for complete search history.

*Primary Examiner*—Kent L Bell
(74) *Attorney, Agent, or Firm*—C. A. Whealy

(57) ABSTRACT

A new and distinct cultivar of *Chrysanthemum* plant named 'Cool Yoigloo', characterized by its upright, outwardly spreading and mounding plant habit; freely branching habit; dense and full plant habit; uniform and freely flowering habit; duplex/decorative-type inflorescences with bright red purple-colored ray florets; and natural season flowering about September 24$^{th}$ in the Northern Hemisphere.

1 Drawing Sheet

Botanical designation: *Chrysanthemum×morifolium.*
Cultivar denomination: 'Cool Yoigloo'.

BACKGROUND OF THE INVENTION

The present invention relates to a new and distinct cultivar of *Chrysanthemum* plant, botanically known as *Chrysanthemum×morifolium,* commercially grown as a perennial garden *Chrysanthemum,* and hereinafter referred to by the name 'Cool Yoigloo'.

The objective of the breeding program is to create new perennial garden-type *Chrysanthemum* cultivars having uniformly rounded plant habit, inflorescences with desirable inflorescence forms, attractive floret colors and good garden performance.

The new *Chrysanthemum* originated from a cross-pollination made by the Inventor in December, 2002, in Salinas, Calif. of a proprietary seedling selection of *Chrysanthemum×morifolium* identified as code number 98-M305, not patented, as the female, or seed, parent with a proprietary seedling selection of *Chrysanthemum×morifolium* identified as code number 00-M476, not patented, as the male, or pollen, parent. The new *Chrysanthemum* was discovered and selected by the Inventor as a single flowering plant within the progeny of the stated cross-pollination in a controlled greenhouse environment in Alva, Fla. in October, 2003.

Asexual reproduction of the new *Chrysanthemum* by vegetative cuttings was first conducted in a controlled greenhouse environment in Alva, Fla. in January, 2004. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Cool Yoigloo'. These characteristics in combination distinguish 'Cool Yoigloo' as a new and distinct garden *Chrysanthemum* cultivar:

1. Upright, outwardly spreading and uniformly mounded plant habit.
2. Freely branching habit; dense and full plant habit.
3. Uniform and freely flowering habit.
4. Duplex/decorative-type inflorescences.
5. Bright red purple-colored ray florets.
6. Natural season flowering occurs about September 24$^{th}$ in the Northern Hemisphere.

In side-by-side comparisons conducted in Alva, Fla., plants of the new *Chrysanthemum* differed from plants of the female parent selection in the following characteristics:

1. Plants of the new *Chrysanthemum* flowered about seven to ten days later than plants of the female parent selection when grown under natural season conditions.
2. Plants of the new *Chrysanthemum* flowered more uniformly than plants of the female parent selection.
3. Plants of the new *Chrysanthemum* had smaller inflorescences than plants of the female parent selection.
4. Inflorescences of plants of the new *Chrysanthemum* had lighter-colored ray florets than inflorescences of plants of the female parent selection.

In side-by-side comparisons conducted in Alva, Fla., plants of the new *Chrysanthemum* differed from plants of the male parent selection in the following characteristics:

1. Plants of the new *Chrysanthemum* flowered about one week earlier than plants of the male parent selection when grown under natural season conditions.
2. Plants of the new *Chrysanthemum* flowered more uniformly than plants of the male parent selection.

3. Plants of the new *Chrysanthemum* and the male parent selection differed in ray floret color as plants of the male parent selection had red-colored ray florets.

Plants of the new *Chrysanthemum* can be compared to plants of *Chrysanthemum×morifolium* 'MN98-E90-15', disclosed in U.S. Plant Pat. No. 14,455. In side-by-side comparisons conducted in Alva, Fla., plants of the new *Chrysanthemum* differed from plants of 'MN98-E90-15' in the following characteristics:

1. Plants of the new *Chrysanthemum* were more mounding than plants of 'MN98-E90-15'.
2. Plants of the new *Chrysanthemum* were more freely branching than plants of 'MN98-E90-15'.
3. Plants of the new *Chrysanthemum* flowered later than plants of 'MN98-E90-15'.
4. Plants of the new *Chrysanthemum* had smaller inflorescences with more ray florets than plants of 'MN98-E90-15'.
5. Inflorescences of plants of the new *Chrysanthemum* were longer-lasting than inflorescences of plants of 'MN98-E90-15'.

Plants of the new *Chrysanthemum* can also be compared to plants of *Chrysanthemum×morifolium* 'Mei Kyo', not patented. In side-by-side comparisons conducted in Alva, Fla., plants of the new *Chrysanthemum* differed from plants of 'Mei Kyo' in the following characteristics:

1. Plants of the new *Chrysanthemum* were smaller than plants of 'Mei Kyo'.
2. Plants of the new *Chrysanthemum* flowered about one month earlier than plants of 'Mei Kyo' when grown under natural season conditions.
3. Plants of the new *Chrysanthemum* and 'Mei Kyo' differed in ray floret color as plants of 'Mei Kyo' had pale lavender-colored ray florets.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*. The photograph at the bottom of the sheet comprises a side perspective view of a typical flowering plant of 'Cool Yoigloo' grown in a container. The photograph at the top of the sheet is a close-up view of typical inflorescences of 'Cool Yoigloo'.

DETAILED BOTANICAL DESCRIPTION

The aforementioned photographs and following observations and measurements describe plants grown in Alva, Fla. during the summer and fall in an outdoor nursery and under conditions and practices which approximate those generally used in commercial garden *Chrysanthemum* production. During the production of the plants, day temperatures averaged 35° C. and night temperatures averaged 24° C. Plants were grown in 15-containers under natural season conditions. Plants were 12 to 13 weeks from planting when the photographs and description were taken. In the following description, color references are made to The Royal Horticultural Society Colour Chart, 1995 Edition, except where general terms of ordinary dictionary significance are used.

Botanical classification: *Chrysanthemum×morifolium* 'Cool Yoigloo'.

Parentage:

*Female, or seed, parent.*—Proprietary seedling selection of *Chrysanthemum×morifolium* identified as code number 98-M305, not patented.

*Male, or pollen, parent.*—Proprietary seedling selection of *Chrysanthemum×morifolium* identified as code number 00-M476, not patented.

Propagation:

*Type.*—Terminal vegetative cuttings.

*Time to initiate roots.*—About four days at temperatures of about 21° C. Time to produce a rooted young plant: About ten to twelve days at temperatures of about 21° C.

*Root description.*—Fine, fibrous; white in color.

*Rooting habit.*—Freely branching.

Plant description:

*Appearance.*—Perennial duplex/decorative-type garden *Chrysanthemum*. Stems upright and outwardly spreading giving a uniformly mounded appearance to the plant. Freely branching habit, about twelve lateral branches each with multiple secondary branches; pinching is not required; dense and full plant habit. Strong and vigorous growth habit.

*Plant height.*—About 26 cm.

*Plant width.*—About 46 cm.

*Lateral branches.*—Length: About 21 cm. Diameter: About 4 mm. Internode length: About 1.4 cm. Strength: Strong. Texture: Pubescent; longitudinally ridged. Color: Close to 146C.

*Leaves.*—Arrangement: Alternate, simple. Length: About 3.4 cm. Width: About 2.5 cm. Apex: Acute. Base: Attenuate. Margin: Palmately lobed, sinuses between lateral lobes mostly parallel. Texture, upper and lower surfaces: Pubescence; veins prominent on lower surface.

*Color.*—Developing and fully expanded foliage, upper surface— Close to 146A; venation, close to 147C. Developing and fully expanded foliage, lower surface— Close to 147B; venation, close to 147C.

*Petiole.*—Length: About 1 cm. Diameter: About 2.5 mm. Texture, upper and lower surfaces: Pubescent. Color, upper and lower surfaces: Close to 147C.

Inflorescence description:

*Appearance.*—Duplex/decorative-type inflorescence form with obovate-shaped ray florets. Inflorescences borne on terminals above foliage. Disc and ray florets arranged acropetally on a capitulum. Inflorescences not fragrant.

*Flowering response.*—Under natural season conditions, plants flower about September 24$^{th}$ in the Northern Hemisphere.

*Postproduction longevity.*—Inflorescences maintain good color and substance for about four weeks in an outdoor nursery. Inflorescences persistent.

*Quantity of inflorescence.*—About 52 inflorescences develop per lateral branch.

*Inflorescence bud.*—Height: About 1 cm. Diameter: About 1.1 cm. Shape: Oblate. Color: Close to 186A to 186B.

*Inflorescence size.*—Diameter: About 3 cm. Depth (height): About 1.1 cm. Disc diameter: About 4 mm. Receptacle diameter: About 1.6 cm. Receptacle height: About 4 mm. Receptacle color: Close to 147B.

*Ray florets.*—Shape: Obovate; inner ray florets, quilled. Orientation: Initially upright, then about 90° from vertical; eventually reflexing. Aspect: Initially incurved, then mostly flat. Length: About 1.9 cm. Width: About 6 mm. Apex: Emarginate. Base: Acute. Margin: Entire. Texture, upper and lower surfaces: Smooth, glabrous; longitudinally ribbed. Number of ray florets per inflorescence: About 260 arranged in about 14 whorls. Color: When opening, upper surface: Close to 187C. When opening, lower surface: Close to 77A to 77B. Fully opened, upper surface: Close to 72A; color resists fading. Fully opened, lower surface: Close to 77B to 77D; color resists fading.

*Disc florets.*—Shape: Tubular, elongated. Length: About 4 mm. Diameter: About 1 mm. Number of disc florets per inflorescence: About 20. Color, immature: Apex: Close to 12A. Mid-section: Close to 12C. Base: Close to 157A. Color, mature: Apex: Close to 13B. Mid-section: Close to 12C. Base: Close to 157C.

*Phyllaries.*—Number of phyllaries per inflorescence: About 24 arranged in about three whorls. Length: About 6 mm. Width: About 4 mm. Shape: Elliptical. Apex: Acute. Base: Truncate. Texture, upper surface: Smooth, glabrous. Texture, lower surface: Pubescent. Color, upper surface: Close to 144A. Color, lower surface: Close to 144B.

*Peduncle.*—Length, terminal peduncle: About 7.4 cm. Length, fourth peduncle: About 4.1 cm. Diameter, terminal peduncle: About 1.5 mm. Angle: Mostly upright to 30° to 45° from vertical. Strength: Strong. Texture: Pubescent. Color: Close to 148C.

*Reproductive organs.*—Androecium: Stamen number: About five per floret. Filament length: About 2 mm. Filament color: Close to 145C. Anther length: About 1 mm. Anther shape: Narrowly lanceolate. Anther color: Close to 13A. Pollen amount: Scarce. Pollen color: Close to 13A. Gynoecium: Pistil length: About 6 mm. Stigma shape: Bi-parted. Stigma color: Close to 7A. Style length: About 2.5 mm. Style color: Close to 145C. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will overwinter in USDA Zones 5 and higher; plants of the new *Chrysanthemum* have been observed to tolerate high temperature of about 38° C.

It is claimed:

1. A new and distinct *Chrysanthemum* plant named 'Cool Yoigloo' as illustrated and described.

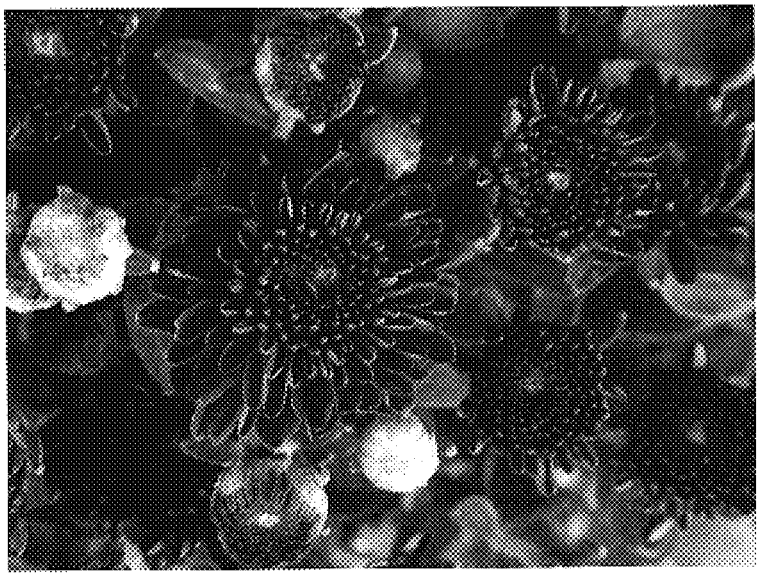
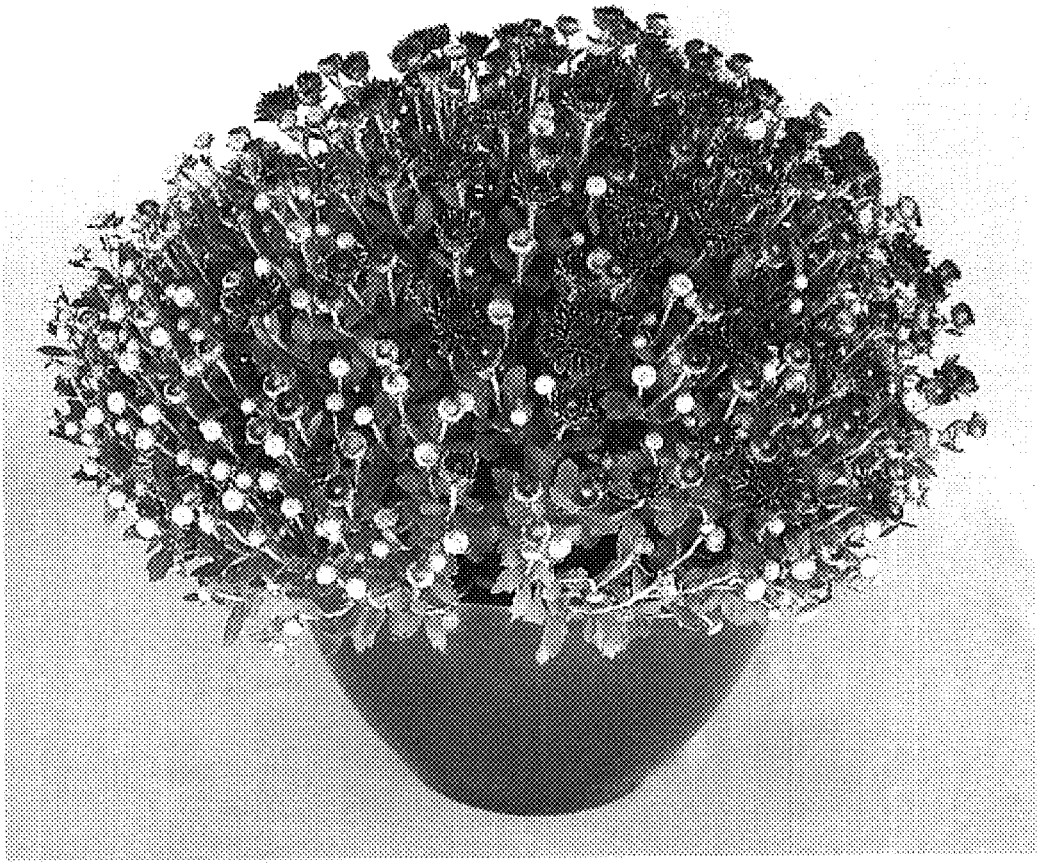

* * * * *